(12) United States Patent
Birkner et al.

(10) Patent No.: US 12,350,633 B2
(45) Date of Patent: Jul. 8, 2025

(54) METHOD AND DEVICE FOR SONICATING A BIOLOGICAL SAMPLE

(71) Applicant: Roche Molecular Systems, Inc., Pleasanton, CA (US)

(72) Inventors: Patrick Birkner, Emmenbruecke (CH); Manfred Holzer, Rikon (CH); Pirmin Hans Loetscher, Hochdorf (CH); Ulf Nilsson, Dozwil (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 18/137,677

(22) Filed: Apr. 21, 2023

(65) Prior Publication Data

US 2023/0249144 A1    Aug. 10, 2023

Related U.S. Application Data

(63) Continuation of application No. 16/376,286, filed on Apr. 5, 2019, now Pat. No. 11,666,873.

(30) Foreign Application Priority Data

Apr. 5, 2018   (EP) ..................................... 18165846
Apr. 4, 2019   (EP) ..................................... 19167291

(51) Int. Cl.
*B01F 31/80*   (2022.01)
*B01F 35/42*   (2022.01)
*B01J 19/10*   (2006.01)
*C12N 13/00*   (2006.01)
*G01N 1/28*    (2006.01)
(Continued)

(52) U.S. Cl.
CPC .............. *B01F 31/80* (2022.01); *B01F 35/42* (2022.01); *B01J 19/10* (2013.01); *C12N 13/00* (2013.01); *G01N 1/286* (2013.01); *B01F 2101/23* (2022.01); *B06B 1/0611* (2013.01)

(58) Field of Classification Search
CPC ................ B01F 11/02; B01F 15/00733; B01F 2215/0037; B01F 31/80; B01J 19/10; B06B 1/0611; C12N 13/00; G01N 1/286
See application file for complete search history.

(56) References Cited

U.S. PATENT DOCUMENTS 4,431,423 A    2/1984   Weyant, Jr.
5,178,602 A    1/1993   Wells
(Continued)

FOREIGN PATENT DOCUMENTS

CN    102728428 A    10/2012
CN    105102110 A    11/2015
(Continued)

*Primary Examiner* — Elizabeth A Robinson
*Assistant Examiner* — Tingchen Shi
(74) *Attorney, Agent, or Firm* — Charney IP Law LLC; Thomas M. Finetti

(57) ABSTRACT

The present disclosure relates to a device for sonicating a biological sample. In one embodiment, a sample tube holder is pivotally suspended in a mount of a sonication device, thus allowing for a rotational degree of freedom and/or lateral movement that provides an optimized contact area between the sonotrode and the sample tube. Also disclosed is a method for sonicating a biological sample using the device described herein.

18 Claims, 7 Drawing Sheets

(51) Int. Cl.
    *B01F 101/23*     (2022.01)
    *B06B 1/06*       (2006.01)

(56)            References Cited

U.S. PATENT DOCUMENTS 6,318,158   B1 *   11/2001   Breen ..................... B01F 31/86
                                                                422/128
    6,686,195   B1      2/2004   Colin et al.
    9,885,729   B2      2/2018   Loo
    9,931,604   B2      4/2018   Felden
   10,677,692   B2      6/2020   Vallayer
 2003/0209427   A1     11/2003   Natan et al.
 2004/0178076   A1      9/2004   Stonas et al.
 2006/0287182   A1     12/2006   Due et al.
 2007/0055152   A1      3/2007   Ukubo et al.
 2012/0238736   A1      9/2012   Harding
 2014/0272938   A1      9/2014   Loo et al.
 2015/0056715   A1      2/2015   Laugharn, Jr.
 2016/0023174   A1      1/2016   Felden
 2017/0261411   A1 *    9/2017   Vallayer ................ B01F 35/92

FOREIGN PATENT DOCUMENTS

CN         105413786   A       3/2016
    CN         216799902   U       6/2022
    EP           2574403   A2      4/2013
    FR           2791697   A1     10/2000
    JP        2007090049   A       4/2007
    JP        2016517516   A       6/2016
    JP        2017535410   A      11/2017
    JP        2002540783   A      12/2022
    WO        2014139630   A1      9/2014
    WO        2016189259   A1     12/2016

* cited by examiner

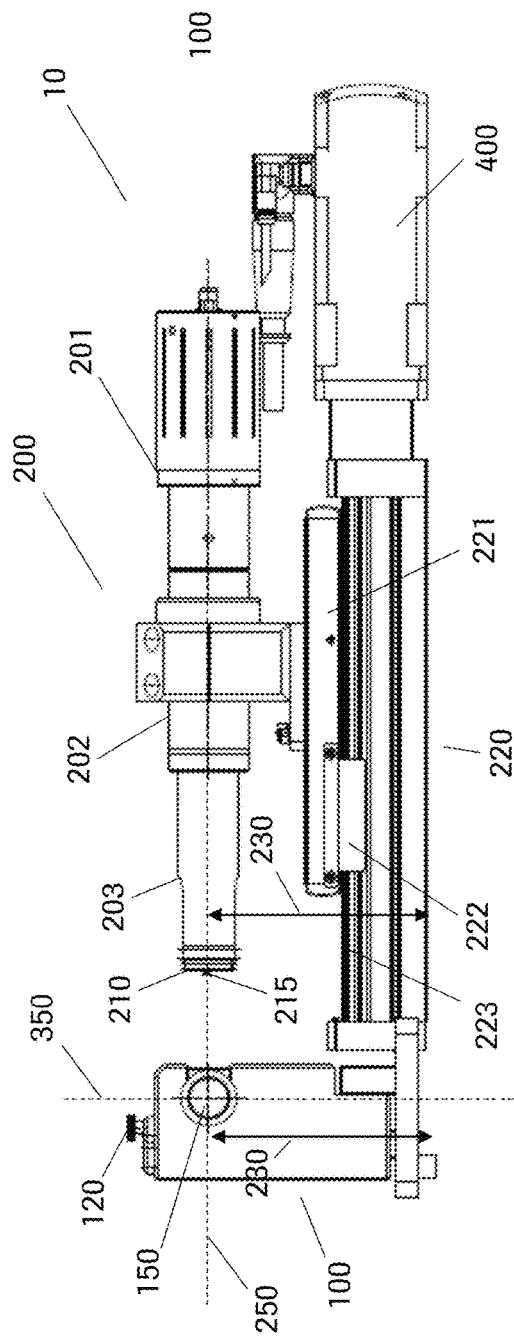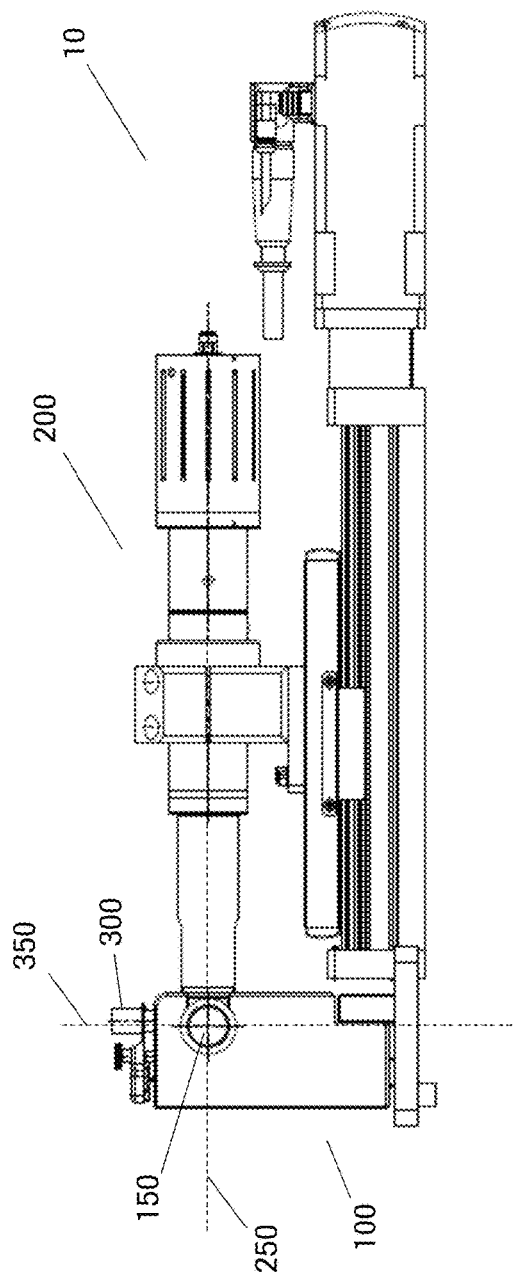

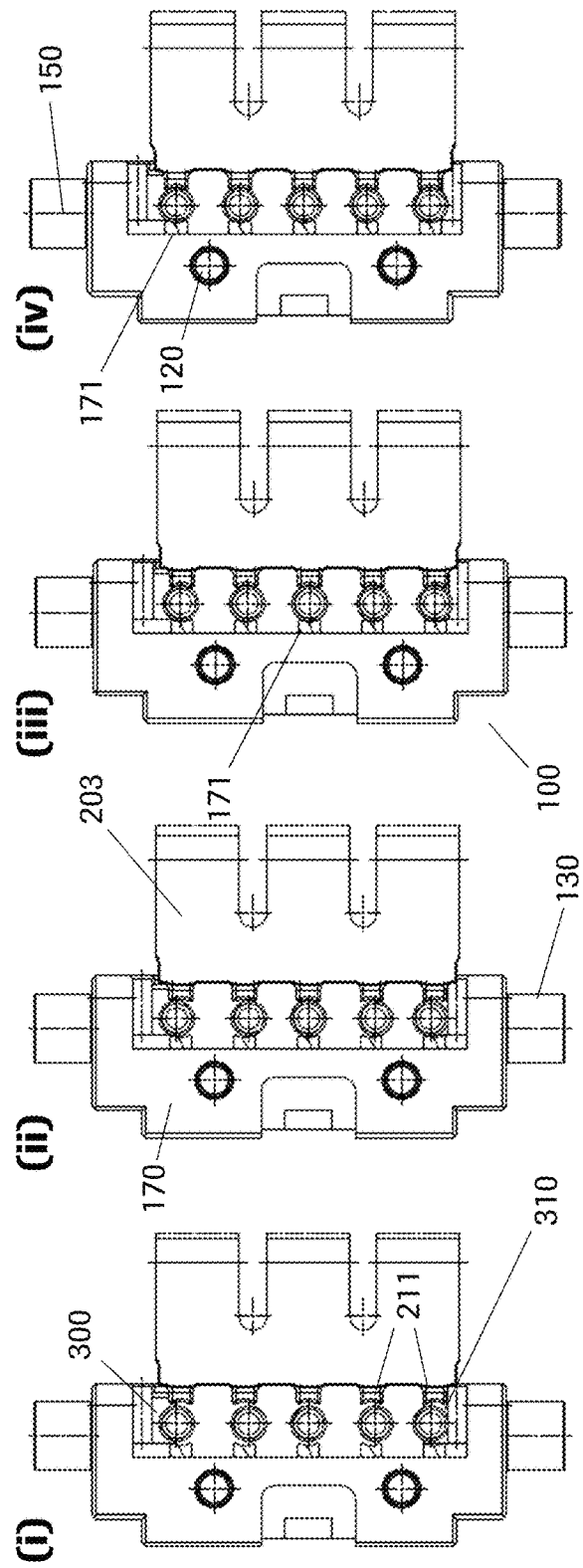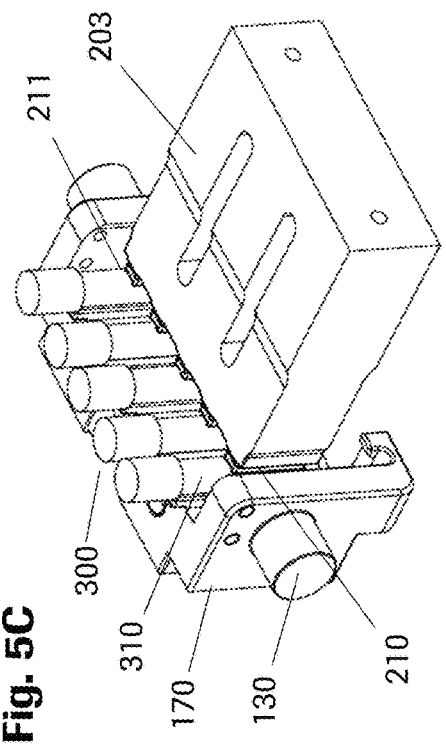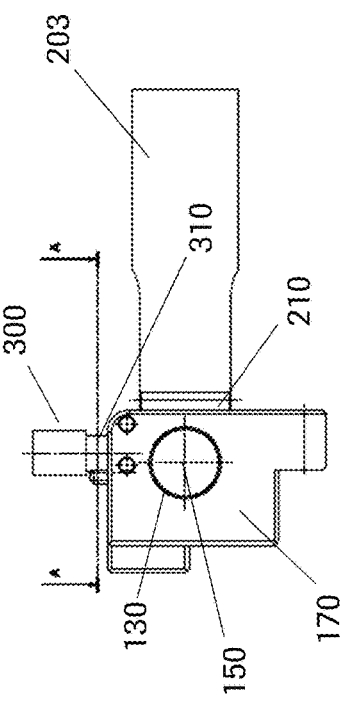

METHOD AND DEVICE FOR SONICATING A BIOLOGICAL SAMPLE

CROSS-REFERENCE TO RELATED APPLICATIONS

This patent application is a continuation of U.S. patent application Ser. No. 16/376,286 filed on Apr. 5, 2019, which applications claims the priority and benefit of European Patent Application No. 19167291.4, filed Apr. 4, 2019, and the priority and benefit of European Patent Application No. 18165846.9, filed Apr. 5, 2018, the contents of which applications are incorporated by reference herein.

FIELD OF THE INVENTION

The present invention belongs to the field of analytical systems for conducting biological or biochemical assays. Within this field, it relates to processing of a liquid biological sample, such as a sample containing biomolecules, with the aid of ultrasonic treatment.

BACKGROUND

Primary biological samples to be analyzed, for example, in the context of in-vitro diagnostics, often require pre-analytical treatment before they can be processed by a biochemical or biophysical analyzer or the like.

For instance, in the context of detecting a pathogen, access of the analytical reagents to a specific analyte within that pathogen may be achieved by a typical preparation step in which viral particles or bacterial cells are lysed such that the respective contents are released, before further measures for the enrichment of the analyte in question may be applied. Standard lysis procedures for most of the common viral particles and bacterial cells are well-stablished and known to the person of skill in the art.

However, certain pathogens require a more rigorous treatment for a successful lysis, including species of the *Mycobacterium tuberculosis* complex (MTBC), in the following also referred to as "mycobacteria". These bacteria are enveloped by a relatively thick and complex cell wall that exhibits a considerably higher robustness than their counterparts found in most other clinically relevant bacteria.

Samples suspected to contain mycobacteria—or other challenging biological material—may be pre-treated by the application of ultrasound, also referred to as sonication or ultrasonication. The approach is generally known and established in the art. However, in some instances, the efficient transmission of ultrasound from a sonication device to a sample can be difficult to achieve. Some approaches in the art rely on sonication while the respective sample vessel is submersed in a liquid medium, often simply water. In that case, the water actually transports the vibration caused by the ultrasonic waves to the sample vessel and thus the sample within, wherein a portion of the primary kinetic energy is usually lost as heat. A more efficient approach involves the direct transfer of ultrasonic energy through physical contact between a sonotrode and the respective vessel. Here, as well, the energy transfer may be impeded if the contact area between the sonotrode and the wall of the sample vessel is not optimal.

Pertinent approaches applied in the art include, for example, U.S. Pat. No. 6,686,195, disclosing a weight controlling the degree of coupling between a sonotrode and a sample vessel. However, the surfaces of sample vessels are usually not ideally even, but exhibit certain material- and/or production-based tolerances that can reduce the effective physical coupling and thus the transmission of ultrasonic energy.

The present disclosure describes an approach that avoids such shortcomings in the art.

SUMMARY

In a first aspect described herein, a device is disclosed for sonicating a biological sample contained in a sample tube. The device includes at least a sample tube holder, a sonotrode, and an actuator.

In one embodiment, the sample tube holder is flexibly suspended from a pivot engaged to a mount within the sonication device. The pivot allows for sample the tube holder to rotate about an x-axis in vertical direction. As long as the sample tube holder is not rotationally deflected, it holds the respective sample tube in a vertical orientation along a z-axis essentially following the direction of gravity and being perpendicular to the x-axis, such that the tube and the sample within are held substantially upright. The sample tube holder has an opening to at least one side to allow for physical contact between the tube and the sonotrode. In some embodiments, the mount is configured to permit movement of the sample tube holder along the x-axis. In other embodiments, the sample tube holder is configured to permit movement of the sample tube within the sample tube holder along the x-axis. In particular embodiments, rotation about the x-axis, movement of the sample tube within the sample holder along the x-axis, and/or movement of the sample holder along the x-axis within the pivot combine to provide an optimal engagement between the sonotrode and the sample tube.

The sonotrode includes a sonication area through which the ultrasound is transmitted to the sample tube upon contacting its essentially round-shaped side wall. The sonotrode and the sample holder are aligned such that the vertical center of the sonication area—along the z-axis—is on the same height as the rotational pivot point—represented by the x-axis—about which the sample tube holder is rotatable. The sonotrode is mounted on a guiding rail such that it can be moved with the aid of the actuator towards or away from the sample holder following a y-axis. The latter is perpendicular to both the x-axis and the z-axis. For sonication, the sonicating area can be brought into contact with the side wall of the sample tube through the respective opening in the sample tube holder. Guidance of this movement is improved by the guiding rail being fixed at one end to the mount for the sample tube holder. A rotational movement of the sample tube and thus the sample tube holder may be induced by the contact of the sonicating area by applying a pre-defined force to the sample holder via the sonotrode, if due to unevenness of the tube's side wall surface or in case of a tapered or conical tube wall a portion of the tube wall comes into contact with the sonicating area prior to the tube wall's other portions, thus optimizing the actual contact area and thereby the transmission of ultrasound. A concave surface of the sonicating area contributes to maximize the contact area in a lateral direction, along the x-axis.

As a further aspect, a method for sonicating a biological sample contained in a sample tube using the device described above is disclosed herein.

SHORT DESCRIPTION OF THE FIGURES

FIG. 2A shows a cross-sectional side view of the sonication device of FIG. 1.

FIG. 2B shows a cross-sectional side view of the sonication device of FIG. 1B, which is in a sonication position.

Figure 1A:
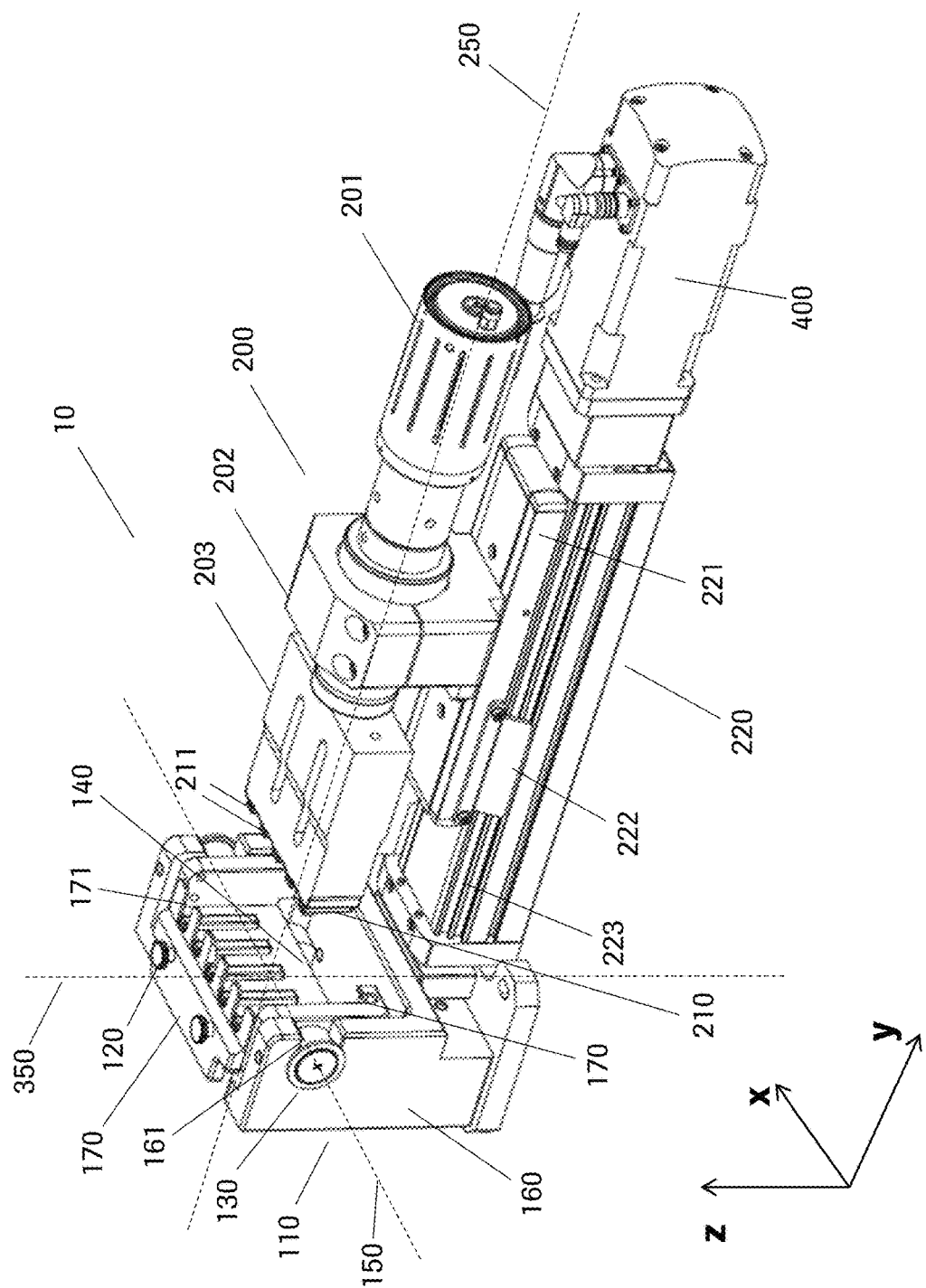
FIG. 1A shows a perspective side view of an embodiment of the disclosed sonication device.

FIG. 5A displays various stages (i-iv) of the movement of the sonotrode towards a sample tube holder with concomitant adjustment of the sample tubes along the x-axis with increasing force.

FIG. 5B shows the rotatable portion of a sample holder.

FIG. 5C shows a perspective view of sample tubes fully engaged with a transmittal unit of a sonotrode.

DETAILED DESCRIPTION

A first aspect described herein is a sonication device for sonicating a biological sample contained in a sample tube with an essentially round-shaped side wall, the sonication device comprising:

- a sample tube holder pivotally suspended in a corresponding mount, allowing for a rotational movement of the sample tube holder in vertical direction about an x-axis being a rotational axis defined by a pivot, wherein the sample tube holder is configured, in the absence of a rotational movement, to hold the sample tube in a vertical orientation along a z-axis being essentially parallel to the direction of gravity and perpendicular to the x-axis, and wherein the sample tube holder comprises an opening towards at least one side;
- a sonotrode comprising a sonicating area for applying ultrasound to the sample tube, the sonicating area comprising a concave surface and being mounted at essentially the same height as the pivot with the x-axis being essentially at the height of the vertical center of the sonicating area, wherein the sonotrode is mounted on a guiding rail for moving the sonotrode along a y-axis perpendicular to the x-axis and the z-axis towards or away from the sample tube holder, wherein the mount for the sample tube holder is fixed to one end of the guiding rail with the opening of the sample tube holder facing the sonicating area such that the sonicating area in a sonication position is in physical contact with a side wall of the sample tube in the sample tube holder;
- an actuator for moving the sonotrode on the guiding rail along the y-axis relative to the sample tube holder.

This sonication device enables the skilled person to optimize the transmission of ultrasonic energy from the sonotrode to the biological sample in the respective sample tube and thereby efficiently treat it, such as, for instance, to lyse robust pathogens like mycobacteria and release their biochemical contents such as nucleic acids.

The interaction of the pivotally suspended sample tube holder with the force-controlled sonotrode allows for a geometrical flexibility, compensating for variations in or on the surface of the sample tube side wall.

In case of unevenness of the tube wall, which may, for instance, be owed to tolerances in the production process of the tube, the contact area between the sonicating area may be reduced as previously mentioned, such that the energy transfer to the tube and thus the biological sample therein may be hampered. In the sonication device described herein, the sample tube which is, in the absence of a rotational movement of the sample tube holder, held essentially vertically along the z-axis, may have a slightly uneven or warped surface. Alternatively or additionally, the tube may in some embodiments have a tapered shape towards its top or, more often, its bottom. For instance, the tube may in some embodiments have a conical shape.

In such or similar cases, the side wall of the sample tube may not form an ideal plane surface. More precisely, along the vertical dimension of the sample tube wall to be contacted with the sonicating area, certain portions of the surface may protrude in relation to other portions. In the case of a rigidly mounted sample tube holder, the sonicating area would be pressed against the tube wall upon moving the sonotrode to the sample tube holder without the possibility to adapt location or orientation. In the case of lesser applied force, the sonicating area would touch the tube wall only at its protruding portion(s), resulting in a non-optimal contact area and the related loss of energy transmission. In the case of higher applied force, on the other hand, the sonotrode may deform the tube, which may endanger the integrity of the sample tube. The latter case may even lead to loss of the sample material, including contamination of the sonication device and posing security risks to the operating personnel in case the biological sample indeed contains pathogens.

However, the sonication device described herein avoids these risks by providing geometrical flexibility for optimizing the contact area between the side wall of the sample tube and the sonicating area. More precisely, in the above-described case, a sonotrode being pressed against the side wall with a pre-defined force would not cause the sample tube holder to remain in the conformation leading to a diminished contact area, but the sample tube holder could rotate around the x-axis defined by the pivot point of the pivot upon contact of the tube wall with the sonication area of the sonotrode. For instance, if the tube has a tapered shape towards its bottom and is held vertically within the sample tube holder, then a vertical, substantially even, sonicating area would usually first contact the upper portion of the tube wall. Upon application of a pre-defined force to the tube wall from the actuator via the sonotrode, the tube can now initiate a rotational movement in which its contacted upper portion follows the movement of the sonotrode, while the lower—so far not contacted—portion is rotated towards the sonicating area opposite to the movement of the sonotrode, since the vertical center of the sonicating area and the pivot point represented by the x-axis are mounted on substantially the same height. As a result, the upper portion of the side wall will remain in physical contact with the sonicating area, while the lower portion—previously not in contact—will be rotated towards the sonicating area and touch it, thereby optimizing the possible contact area between the tube wall and the sonicating area. In this position, the "sonication position", both the rotational movement of the sample tube holder and the translational movement of the sonotrode have reached an arresting point, such that the optimized contact area is maintained for and throughout the sonication process, as long as the force applied from the sonotrode to the sample tube and thus the sample tube holder is kept constant. The sonication position may, however, also be reached without a rotational movement, in case the contact area is already optimal upon primary contact of the sonicating area with the side wall of the sample tube.

Terms

The term "sonication", as used herein, means a process of converting an electrical signal into a physical vibration—in this case ultrasound—that can be directed toward the biological sample. An ultrasonic electric generator creates a primary signal powering a transducer. The signal has, in some embodiments, a frequency of from 20 kHz, 35 kHz, or 50 kHz to 75 kHz, 100 kHz, or 250 kHz. In some embodiments, the frequency is about 20 kHz. Via intermediate elements, such as crystals that may be piezoelectric crystals stacked within the sonotrode, this signal is transformed into mechanical vibration, which process can also be referred to as conversion. The sonotrode may be a rod such as a metal rod, and it may for instance have a cylindrical or conical shape. The frequency of the current may be chosen to be the resonant frequency of the sonotrode such that the latter vibrates lengthwise with standing waves at its resonant frequency. The vibration may be amplified, for instance, by a booster, before transmitting it to a sample tube via a transmittal unit comprising the sonicating surface of the sonotrode. The rapid movement of the sonicating face creates ultrasound waves migrating through the biological sample in the sample tube, inducing pressure variations that grow and collapse. The corresponding kinetic energy is used for processing the biological material in the sample, for instance, in order to lyse cells such as mycobacterial or other cells or viruses of clinical interest.

A "sonotrode" usually comprises a stack of piezoelectric transducers attached to a tapering metal rod. Other suitable materials and shapes are known to the person of skill in the art. The end of the rod is applied to the working material. An alternating current oscillating at ultrasonic frequency is applied by a separate power supply unit to the piezoelectric transducers. The current causes them to expand and contract.

"Biological target material" or "biological material", in the sense of this disclosure, comprise all kinds of biological molecules, for example proteins or nucleic acids, but also other molecules occurring in nature or being derivatives or synthetic analogues or variants thereof. Furthermore, the term "biological material" comprises viruses and eukaryotic and prokaryotic cells. In some embodiments, the biological target material is nucleic acids such as DNA, RNA or PNA. The DNA can be, for instance, viral DNA, genomic DNA or plasmid DNA. The biological target material can be native or modified. Native biological material is not irreversibly altered as compared the respective naturally occurring biological material, such as e.g. DNA or RNA isolated from organisms. Modified biological material comprises biotinylated molecules such as nucleic acids or proteins, or the like.

As used herein, the term "biological sample" refers to biological material that may potentially contain an analyte of interest. In embodiments where the "biological sample" is a "liquid biological sample", the sample can be derived from any biological source, such as a physiological specimen, including blood, saliva, ocular lens fluid, cerebrospinal fluid, sweat, urine, stool, semen, vaginal fluid, milk, ascites fluid, mucous, synovial fluid, peritoneal fluid, amniotic fluid, tissue, cultured cells, sputum, or the like. The test sample can be pretreated prior to use, such as preparing plasma from blood, diluting viscous fluids or diluting in general, lysis or the like. Methods of treatment can involve filtration, distillation, concentration, inactivation of interfering components, and the addition of reagents. A biological sample may be used directly as obtained from the source or used following a pretreatment to modify the character of the sample. In some embodiments, an initially solid or semi-solid biological material is rendered liquid by dissolving or suspending it with a suitable liquid medium. In some embodiments, the biological sample is suspected to contain a certain antigen or nucleic acid.

A "sample tube" means a vessel configured to hold the biological sample. A sample tube generally has a top and a bottom portion, wherein the bottom portion is typically closed while the top portion comprises an opening for introducing or removing the sample, reagents, or the like. The opening may be sealable, for instance, by a lid which may be removable. Suitable lids are known to the skilled person and include screw caps, form- or press-fit caps, sealing foils, and the like. A sample tube, as used herein, has a generally elongate shape, such as a cylindrical, conical, or similar shape. It comprises a bottom wall and a side wall. The latter may be a continuous side wall or multiple side walls separated by angles. The inside surface of a sample tube is usually inert such that it does not interfere, for instance, with analytical or preparative chemical reactions taking place within the tube. Sample tubes used in the devices and methods disclosed herein usually have a length of from 2 cm, 3.5 cm, or 5 cm to 10 cm, 15 cm or 20 cm. In some embodiments, the length from bottom to top is about 7.5 cm. The width or diameter (side wall to side wall) is, in some embodiments, from 0.5 cm, 1 cm or 1.5 cm to 2 cm, 3.5 cm, 5 cm, in a more specific embodiment it is about 1 cm.

The "sample tube holder" refers to a device for receiving a sample tube. A sample tube holder can be a single-tube holder or a multiple-tube holder. Multiple-tube holders include, for instance, racks for 2, 3, 4, 5, 10, or more tubes. In some embodiments, the sample tube holder has a slot for inserting the sample tube and holding it in a specific position. In the context described herein, the sample tube holder essentially fixes the sample tube, when inserted, in a specific orientation. In the absence of a rotational deflection of the sample tube holder, the sample tube holder holds the sample tube in an essentially vertical position. In some embodiments, the sample tube is form-fit within the sample tube holder, thus providing a tight fit in a fixed orientation.

"Pivotally suspended", in the context described herein, means that an object such as the removable sample tube holder is engaged to another object such as the corresponding mount with a rotational degree of freedom. The sample tube holder described herein can be rotated about the x-axis as a pivot point while it is suspended from the mount.

The sample tube holder described herein is in some embodiments removable, wherein "removable" means that it can be separated from its corresponding mount without any of the two components being destroyed. For instance, the sample tube holder may comprise a hinge that can be flexibly engaged to a corresponding bearing comprised by the respective mount while allowing for a rotational degree of freedom. For example, after sonication of the sample in question, the sample tube holder may be removed from the mount and the sonication device by disengaging the hinge of the sample tube holder from the corresponding bearing of the mount. The sample tube holder may thus be transferred, for instance, to a biochemical analyzer or analytical module. Also, the sample tubes may be filled, prepared or otherwise processed outside of the sonication device while already held by the sample tube holder, thus both simplifying the workflow and reducing the risk of contamination due to, for example, spilling of sample or reagents within the sonication device.

In some embodiments, the mount for the sample tube holder comprises two parts, in some embodiments even more than two. In a more specific embodiment, the mount for the sample tube holder comprises an immobile base portion and a rotatable portion comprising the pivot and a base for holding the sample tube holder, wherein the pivot is a hinge pivotally suspended within a corresponding pivot bearing of the immobile base portion.

The advantages of such a two-parted arrangement of the mount include that, for instance, if the rotatable portion shows signs of abrasion, then this portion could be removed and replaced without having to affect the immobile base portion. The latter can thus be permanently fixed to the bottom of the sonication device as an integral part thereof.

In order to optimize alignment of the sonicating area of the sonotrode with the biological sample contained in the sample tube when present in the sample tube holder in its corresponding mount, the mount of the sonication device disclosed herein comprises in some embodiments a height adjustment for adjusting the position of the sample tube in the sample tube holder on the z-axis. In this manner, a biological sample, particularly a liquid or partially liquid sample contained mostly in the bottom portion of the tube due to the effect of gravity, can be brought to the height of the sonicating area of the sonotrode in the sonication position. This may avoid situations in which the sonicating area touches a part of the tube wall where no or only little sample is located, which may render sonication of the sample more difficult. Means for adjusting the height of the sample tube within the sample tube holder include, for instance, a spring, a coil, a screw mechanism, an air buffer, an actuator, or the like. In some embodiments, the height adjustment is manually operable. In other embodiments, the height adjustment comprises an automated mechanism.

The "guiding rail" of the sonication device described herein can be embodied by any suitable structure providing guidance to the movement of the sonotrode in a defined orientation. In the simplest case, the guiding rail is a straight (one-dimensional) structure along which the sonotrode is moved back and forth by the actuator. However, the guiding rail may also extend across a second or third dimension where appropriate. For instance, two or more sample tube holders mounted next to each other may benefit from a guiding rail having a branching point, such that the sonotrode may be guided to each of the sample tube holders in their respective mounts individually, as the application may require. The guiding rail may in some embodiments comprise a frame in which the sonotrode is suspended. Also in some embodiments, the guiding rail may be embodied by a tunnel holding the sonotrode. In some embodiments, the guiding rail of the sonication device described herein comprises a sled. In a more specific embodiment, the sled is mounted on a railing and carries the sonotrode on its top portion.

The sonication device described herein may comprise a control unit and/or a data management unit.

A "control unit" controls an automated system in a way that the necessary steps for the processing protocols are conducted by the automated system. That means the control unit may, for example, instruct the automated system to conduct certain pipetting steps with a pipettor to mix the liquid biological sample with reagents, or the control unit controls the automated system to incubate the biological sample or reagents or mixtures of both for a certain time at a certain temperature, or the control unit controls the precise movements of the sonotrode of the sonication device described herein, or other movements or related parameters. The control unit may receive information from a data management unit (DMU) regarding which steps need to be performed with a certain sample. In some embodiments, the control unit might be integral with the data management unit or may be embodied by a common hardware. The control unit may, for instance, be embodied as a programmable logic controller running a computer-readable program provided with instructions to perform operations in accordance with a process operation plan. In particular, the control unit may include a scheduler, for executing a sequence of steps such as the movements described above within a predefined time. The control unit may further determine the order of samples to be processed according to the assay type, urgency, and the like. The control unit may also receive data from a detection unit related to a measurement of a parameter of the sample.

A "data management unit" is a computing unit for storing and managing data. This may involve data relating to the liquid sample to be processed by the automated system, or data relating to the steps to be carried out by the sonication device described herein. The data management unit may be connected to an LIS (laboratory information system) and/or an HIS (hospital information system). The data management unit (DMU) can be a unit within or co-located with the automated system it interacts with. It may be part of the control unit. Alternatively, the DMU may be a unit remotely located from the automated system. For instance, it may be embodied in a computer connected via a network to the automated system.

In order for the sonotrode to initiate a defined rotation of the sample tube holder about the x-axis, it may be advantageous to control and—if required—adapt the force that is exerted from the actuator to the sonotrode and thus the sample tube in its corresponding holder.

Therefore, in some embodiments of the sonication device described herein, the actuator is configured to apply a variable force to the sonotrode. In some embodiments, the actuator is configured to apply a force of 10 N, 50 N, 100 N, or 500 N, to 750 N, 1000 N, 2500 N, or 5000 N to the sonotrode. In a more specific embodiment, the force is about 800 N.

Controlling and varying this force may be of advantage, for instance, if different types of sample tube holders are to be processed in the same sonication device. Based on, for example, the mass of the sample tube holder, it may require an increased force to initiate the rotational movement about the x-axis, and the reset force may be greater than in the case of a lighter sample tube holder. Furthermore, different types of sample tubes may be used, wherein certain types may have a more delicate structure than others. Hence, it may be useful to reduce the applied force in order not to compromise the integrity of the more pressure-sensitive tube species.

To the benefit of parallelization and increased throughput, the sonication device described herein may be configured to support and process more than one sample tube at a time. This may require certain adaptations of the sample tube holder and/or the sonotrode, some of which are disclosed herein as exemplary embodiments.

Thus, in some embodiments of the sonication device described herein, the sample tube holder is configured to hold multiple sample tubes and the sonicating area comprises one or more sub-areas with a concave surface. In some embodiments, the sonicating area comprises the same number of sub-areas with a concave surface as the number of sample tubes that the sample tube holder is configured to hold.

A further aspect of the present disclosure is a method for sonicating a biological sample contained in a sample tube with an essentially round-shaped side wall using the sonication device disclosed herein, the method comprising the following steps:

a) Inserting the sample tube into the sample tube holder, and inserting the sample tube holder into the corresponding mount of the sonicating device, wherein the order of these inserting steps is interchangeable;

b) Moving the sonotrode along the y-axis and the guiding rail towards the sample tube holder via the actuator until the sonicating area contacts the side wall of the sample tube through the opening;

c) Applying a pre-defined force from the actuator via the sonotrode to the sample tube and thus the sample tube holder along the y-axis such that the sonicating area contacts the sample tube side wall and pushes the sample tube against the inner wall of the sample tube holder or a rotatable portion thereof, thereby firmly holding the sample tube in place and adjusting its position along the x-axis by centering them with the concave surface comprised by the sonicating area, the movement of the sonotrode further causing a rotational movement of the sample tube holder about the x-axis in case the side wall is not aligned with the surface of the sonicating area until reaching an arresting point, resulting in an enlarged contact area between the sonicating area and the sample tube side wall;

d) Applying ultrasound to the sample tube from the sonotrode through the contact area between the sonicating area and the sample tube side wall.

Regarding step a), it may in some embodiments be of advantage to prepare the sample tube in the sample tube holder outside the sonication device, as described previously. For instance, multiple sample tubes may be placed into a multi-tube sample tube holder and pre-processed, for example, manually by laboratory personnel. Such a step could involve addition of a liquid biological sample, along with or without a reagent, to the multiple sample tubes and capping the latter. In the next step, the laboratory personnel may conveniently place all the pre-processed sample tubes within the same sample tube holder into the sonication device by engaging the sample tube holder to the corresponding mount. This facilitates the overall workflow and may lead to a reduced turnaround time. Alternatively, the sample tube holder may be placed into the sonication device first. As an example, one of the multiple tubes described before needs to be replaced, or an additional tube needs to be added, then the sample tube holder may be left inside the sonication device with the other tubes to be sonicated, while the individual tube can be replaced or added.

As in the case of the sonication device described herein, it may be advantageous to adjust the pre-defined force in step c) depending on the type of sample tube and/or sample tube holder.

In some embodiments of the method described herein, step a) further comprises adjusting the height of the sample tube within the sample tube holder.

Also in some embodiments of the method described herein, the sample tube holder is configured to hold multiple sample tubes and the sonicating area comprises one or more sub-areas with a concave surface. The advantages of such embodiments include the increase of throughput, as described in connection with the sonication device disclosed herein.

As set out above, vertical alignment of the sample in the sample tube on the one hand and the sonicating area on the other hand can be advantageous with regard to efficiency of the sonication of the biological material in the sample. The same accounts for the lateral alignment by virtue of the concave surface of the sonicating area or its sub-areas, respectively.

All other specific embodiments of the method disclosed herein also apply to the device disclosed herein.

EXEMPLARY EMBODIMENTS

The following Examples are meant to illustrate specific embodiments of the method and device disclosed herein, while they are not limiting.

The schematic drawing of FIG. 1A depicts a perspective side view of an embodiment of the sonication device (10) disclosed herein. In this embodiment, the sample tube or tubes (300) and the sample tube holder (100) are omitted for the sake of better visibility of the other components. Among the shown components is the corresponding mount (110) for the sample tube holder. The mount (110) in this embodiment comprises an immobile base portion (160) and a rotatable portion (170) comprising a base (171) for holding, in this case, a sample tube holder (100) with five individual sample tubes (300). The rotatable portion (170) also comprises at both sides a pivot (130) whose pivot point defines the x-axis (150) about which the rotatable portion (170) and thus the sample tube holder (100), when inserted, is rotatable. The pivot (130), here depicted as a hinge, is held by a corresponding pivot bearing (161) of the immobile base portion (160) of the mount. The rotatable portion (170) of this embodiment further has a height adjustment (120), in the depicted case a manually operable mechanism based on screws (120) for lifting or lowering the base (171) holding the sample tube holder (100). In this embodiment, the entire sample holder (100) can thus be vertically adjusted, such that the sample tubes (300) and the biological samples contained therein can be adjusted to the height of the sonicating area (210) of the sonotrode (200). Turning to the latter, it can be seen that the sonication area (210) of this embodiment comprises five sub-areas (211) for the maximum load of five individual sample tubes (300). This sonicating area (210) of the sonotrode (200) faces towards an opening (140) to one side of the sample tube holder (100, not shown) such that it can be brought into physical contact with the sample tube or tubes (300) through the opening (140). The guiding rail (220) of the sonotrode (200) of the present embodiment comprises a sled (221) on which the sonotrode (200) is mounted, with the sled (221) itself being mounted via a connector (222) to a railing (223). This guiding rail (220) arrangement provides movability of the sonotrode (200) along the y-axis (250). It can be seen that this movability is one-dimensional, such that the sonotrode (200) can be moved with the help of an actuator (400) towards or away from the mount (110) for the sample tube holder (100), while the guiding rail (220) is fixed at one end to said mount (110), in this embodiment to its immobile base portion (160). The mount (110) is essentially in alignment with the z-axis (350), essentially parallel to the direction of gravity. Also visible in this depiction is the composition of the sonotrode (200) of the embodiment shown here. The piezoelectric elements are contained within the converter (201) transforming a primary electrical signal into mechanical vibration. The latter is amplified by the subsequent booster (202), before the following transmittal unit (203) transmits the energy via its sonicating area (210).

Figure 1B:
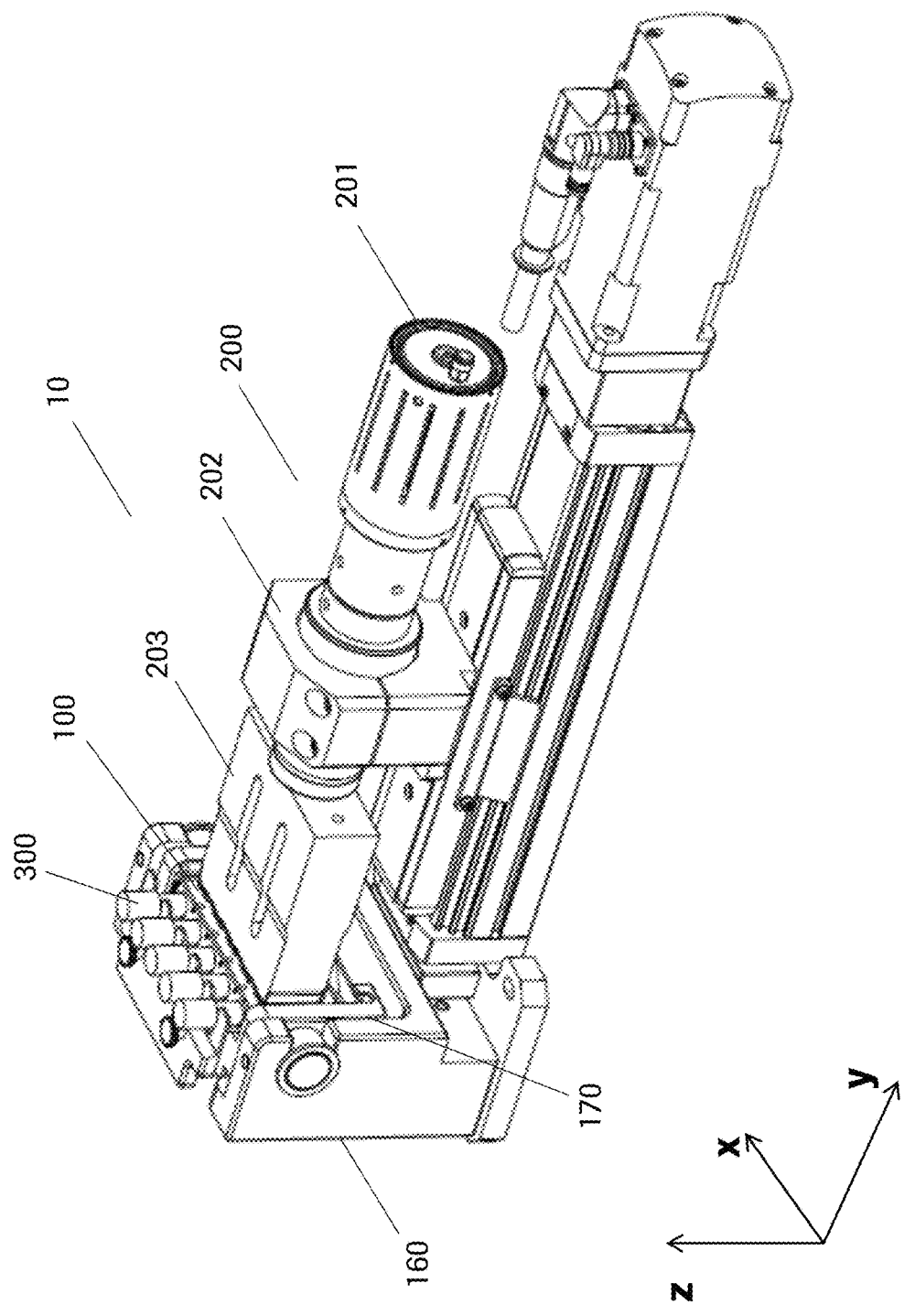
FIG. 1B shows the sonication device of FIG. 1A in a sonication position.

FIG. 1B shows the sonication device (10) of FIG. 1A in a sonication position. The sonotrode has been moved towards the sample tube holder (100) mounted to the rotatable part (170) of the corresponding mount (110). The sonicating area (210) with its individual sub-areas (211) are in contact with the sample tubes (300) held within the sample tube holder (100) through the corresponding openings (140).

Turning to FIG. 2A, the sonication device (10) of FIG. 1 is now depicted as a cross-sectional side view. The sonicating area (210) is mounted at essentially the same height as the pivot (130). Also visible is the vertical dimension of the sonicating area (210), along with its vertical center (215) that is mounted at the same height as the pivot point defined by the x-axis (150).

As in FIG. 1B, a depiction of the sonication device (10) from the cross-sectional side-perspective of FIG. 2A is shown in a sonication position in FIG. 2B.

FIG. 3 and FIG. 4 provide an illustration of an embodiment of the method described herein using the sonication device (10) described herein as depicted in the foregoing Figures.

Figure 3A:
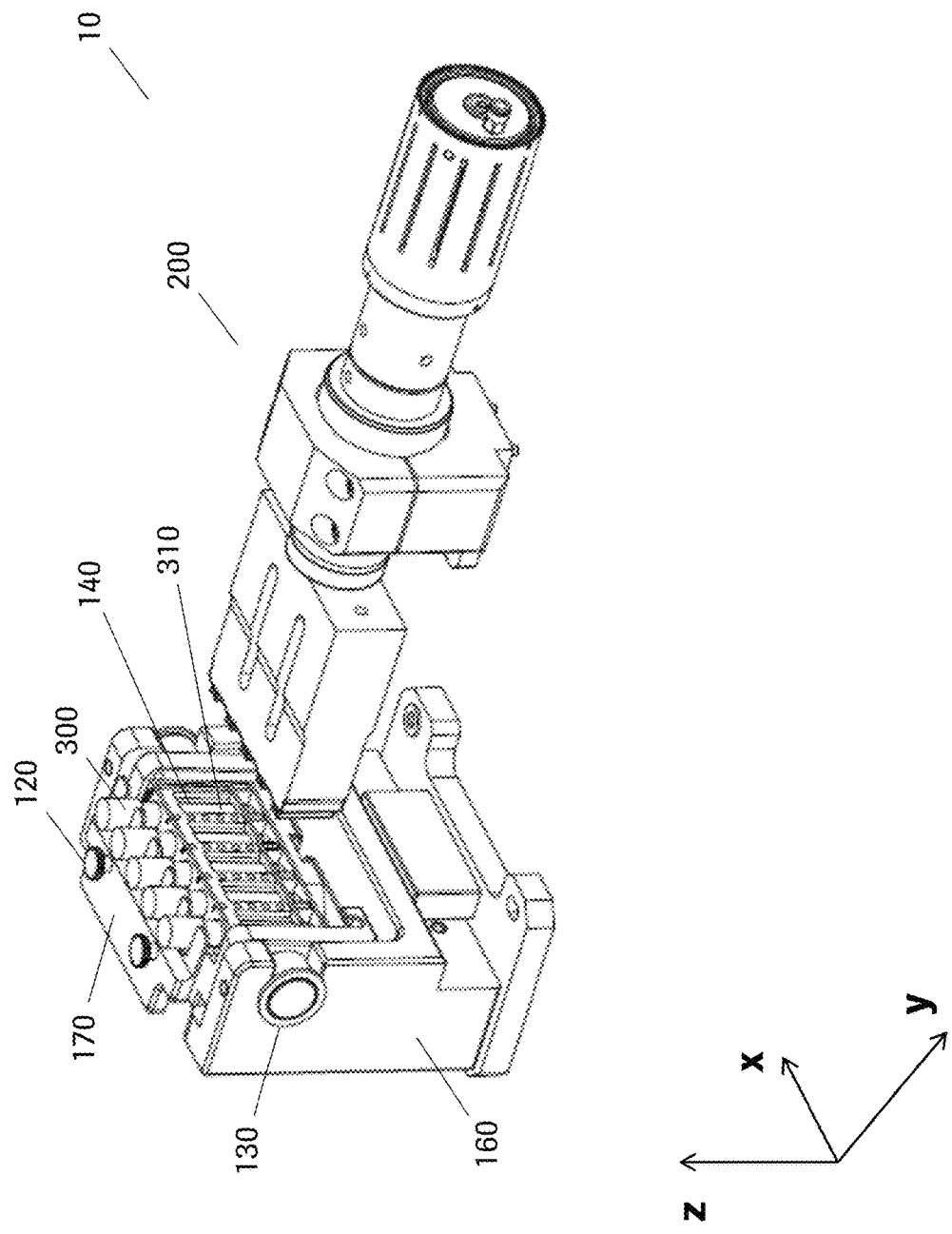
FIG. 3A shows a perspective side view of the sonication device of FIG. 1A without the guide rail shown.
Figure 4A:
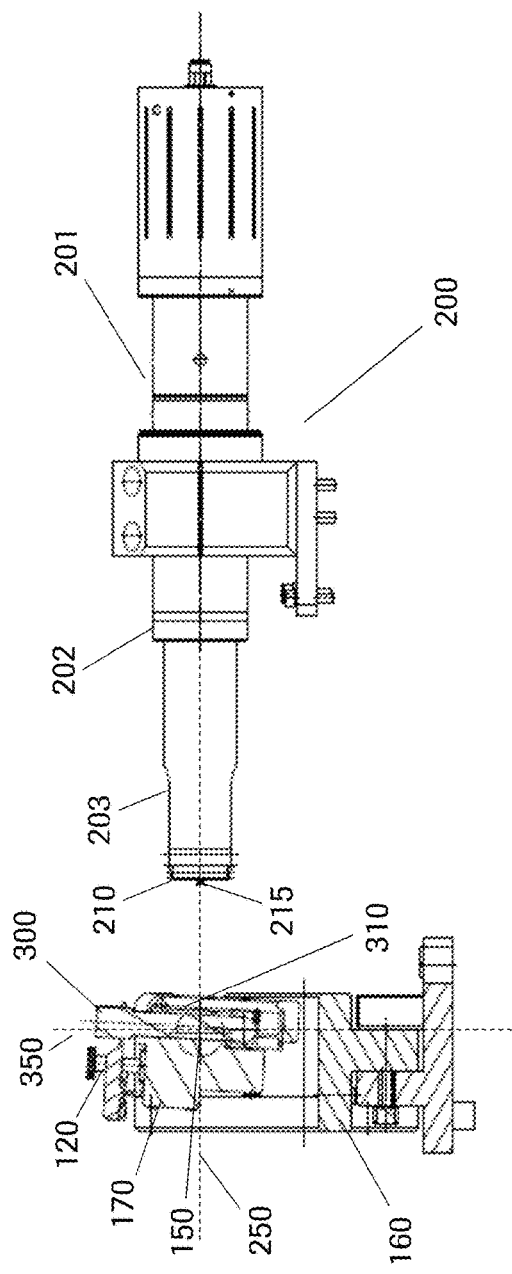
FIG. 4A shows a cross-sectional view of the sonication device of FIG. 3A.

FIG. 3A shows a perspective side view of the above-depicted embodiment of the sonication device (10) described herein. The guiding rail (220) has been omitted for the sake of better visibility of the mount (110) with the inserted sample tube holder (100). As in FIGS. 1A and 2B, the sonotrode (200) is located in a remote position, in which there is no direct physical contact between the sonicating area (210) and the side wall (310) of the sample tube (300). In contrast to the foregoing Figures, the rotatable portion (170) of the mount (110) is slightly tilted against the z-axis (350), which can be seen in more detail in the corresponding cross-sectional side view of FIG. 4A.

Figure 3B:
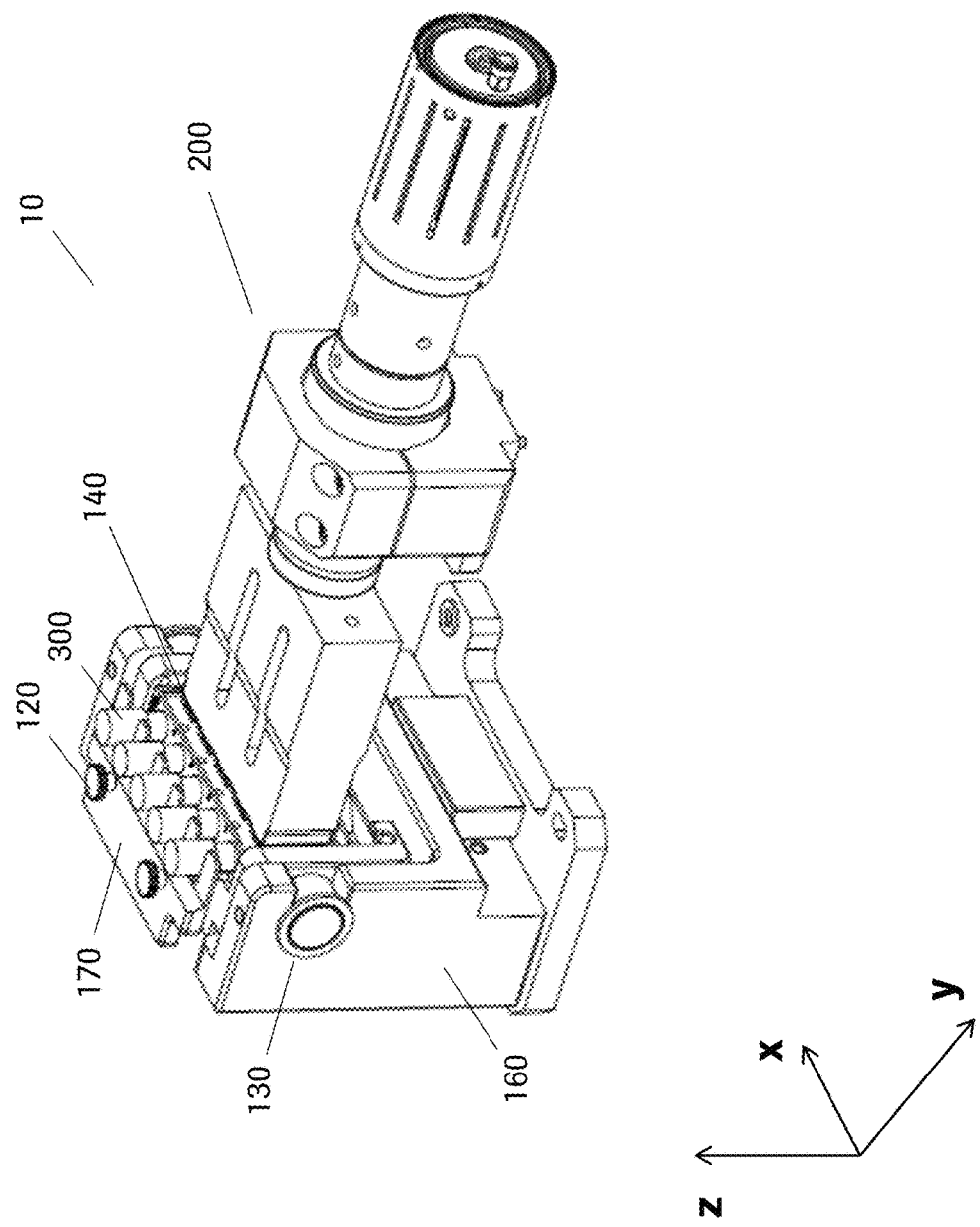
FIG. 3B shows a perspective side view of the sonication device of FIG. 1B, which is in a sonication position, without the guide rail shown.
Figure 4B:
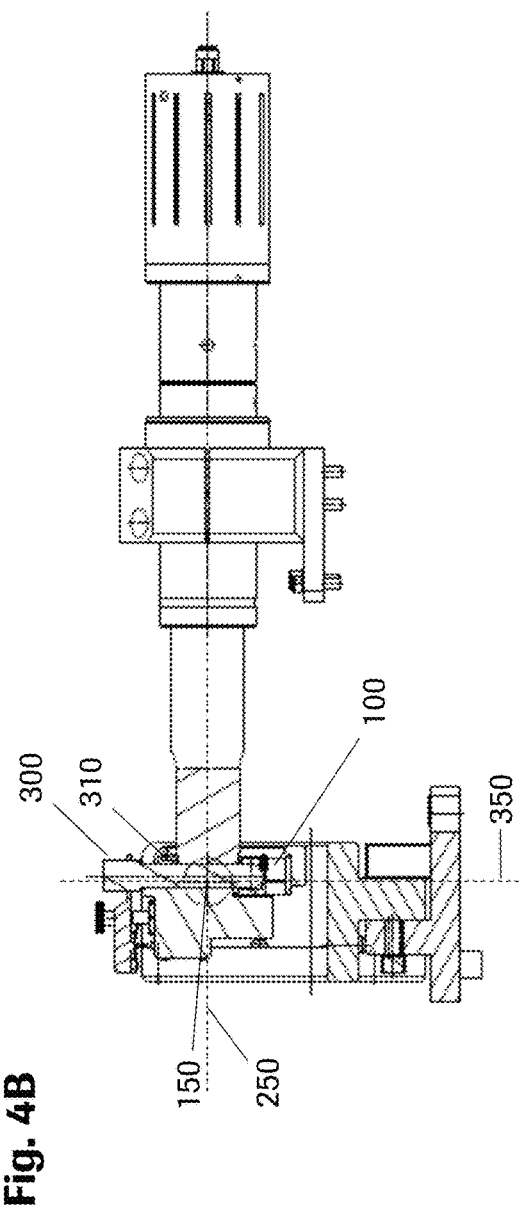
FIG. 4B shows a cross-sectional view of the sonication device of FIG. 3B, which is in a sonication position.

The configuration of the sonication device (10) of this embodiment in a sonication position is shown in FIG. 3B and FIG. 4B. Upon contact of the sonicating area (210) of the sonotrode (200) with the side wall (310) of the sample tubes (300) while applying a pre-defined force, the portion of the side wall (310) located above the vertical center (215) of the sonicating area (210) and thus the x-axis (150) being the pivot point of the pivot (130) is rotated counter-clockwise about the x-axis (150). As the sample tubes (300) are tightly fitted inside the sample tube holder (100), and the sample tube holder inside the rotatable part (170) of the corresponding mount (110), the rotatable part (170) follows this rotational movement of the sample tubes (300) until reaching the arresting point seen in present FIGS. 3B and 4B. In the resulting sonication position of this embodiment, the sample tubes (300) are vertical and thus parallel to the z-axis (350). This is due to the circumstance that the side walls (310) of the sample tubes (300) shown in FIGS. 3 and 4 do not exhibit any substantial unevenness, and the sonicating area (210) of the sonotrode (200), including the sonicating sub-areas (211) are aligned parallel to the z-axis (350). Hence, the vertical position of the sample tube (300) in the sample tube holder (100) and the rotatable part (170) of the mount (110) represents the position in which the sample tube side wall (310) and the sonicating area (210) possess the optimal contact area, thus facilitating efficient transfer of ultrasonic (kinetic) energy from the sonotrode (200) to the biological sample. In the embodiment shown here, this means that each of the individual sub-areas (211) is in contact with the side wall (310) of each corresponding sample tube (300).

The drawings of FIGS. 5A-C provide further insight to the mechanism of adjusting the sample tube (300) along the x-axis (250), displaying the sample tube holder (100)—more precisely, in the depicted embodiment, the rotatable portion (170) of it—from various perspectives.

FIG. 5A depicts the movement of the transmittal unit (203) of the sonotrode (200) with its sonicating area (210) towards the sample tube holder (100) in a chronological order. The rotatable portion (170) of the sample tube holder (100) is viewed from above as a cross-section at the height defined by plane "A" as seen in FIG. 5B.

The first depicted stage of the movement is shown in FIG. 5A(i). The sonicating area (210), in this embodiment comprising five distinct sonicating sub-areas (211), is already located at a short distance to the side walls (310) of the sample tubes (300) held in the rotatable portion (170) of the sample tube holder (100). It can be seen that most of the sample tubes (300) are not aligned with their corresponding sonicating sub-areas (211) along the x-axis (150). Turning to FIG. 5A(ii), the sonicating sub-areas (211) come into physical contact with the side walls (310) of the corresponding sample tubes (300). By virtue of their concave surface, the sonicating sub-areas (211) confer a movement of the sample tubes (300) along the x-axis (150) towards the center of each corresponding sub-area (211), which has progressed further in the depiction of FIG. 5A(iii). Through continued application of the pre-defined force moving the sonotrode (200) with its transmittal unit (203) towards the sample tube holder (100) along the y-axis (250), the concave sonicating sub-areas (211) effectuate a sliding movement of the sample tubes (300) with their essentially round-shaped side walls (310). It can be seen that the embodiment shown here involves supporting elements (171) protruding from the inner back wall of the rotatable portion (170) of the sample tube holder (100). These protrusions exhibit a concave surface in analogy to the surface of the sonicating sub-areas (211) and contribute to aligning the sample tubes (300) in x-direction. However, the concave surfaces of the sonicating sub-areas (211) are capable of bringing about the alignment also by pressing the sample tubes (300) against a flat surface of the back wall. Hence, in some embodiments, the back wall does not comprise the supporting elements (171) shown here. An end point is reached in FIG. 5A(iv), where the sample tubes (300) are aligned along the x-axis (150) with their corresponding sonicating sub-areas (211). The person skilled in the art will appreciate that the sonicating area (210) need not necessarily be embodied, as depicted here, as a surface supporting individual sonicating sub-areas (211). For instance, the sonicating area (210) may have a single concave surface without any protruding sub-areas (211) which may, for example, be arranged for engaging a single sample tube (300). In some embodiments, the rotatable part (170) of the mount (110) may be flexibly suspended such that one or more degrees of freedom are given in which the rotatable part (170) may contribute to optimal alignment of the components involved. For example, the pivot can slide within the pivot bearing (161) of the immobile base portion (160) of the mount along the x-axis to provide additional lateral movement of the tube or tubes to optimize contact between the sonotrode sonicating sub-areas and the sample tube or tubes.

The invention claimed is:

1. A sonication device for sonicating one or more biological samples in at least two sample tubes, the at least two sample tubes each having an essentially round-shaped side wall, the sonication device comprising:
  a. a sample tube holder pivotally suspended in a mount configured to hold the at least two sample tubes, wherein the mount permits rotational movement of the sample tube holder about an x-axis, wherein the sample tube holder is configured, in the absence of a rotational movement about the x-axis, to hold the sample tube in a substantially vertical orientation along a z-axis, the z-axis being perpendicular to the x-axis, and wherein the sample tube holder comprises an opening on at least one side, wherein the sample tube holder comprises a support element having at least two concave surfaces, where each concave surface is configured to individually contact a side wall of each of the at least two sample tubes, and wherein the support element protrudes from a back wall of the sample tube holder;
  b. a sonotrode comprising a transmittal unit having at least two sonicating areas for applying ultrasound to a side wall of each of the at least two sample tubes, the at least two sonicating areas each comprising a concave surface, wherein the sonotrode is mounted on a guiding rail, wherein the mount is fixed to one end of the guiding rail such that the opening on the at least one side of the sample tube holder faces the sonicating areas; and,
  c. an actuator for moving the sonotrode on the guiding rail along a y-axis towards or away from the sample tube holder.

2. The sonication device of claim 1, wherein the sample tube holder is removable.

3. The sonication device of claim 1, wherein the mount for the sample tube holder comprises an immobile base portion and a rotatable portion comprising a pivot and a base for holding the sample tube holder, wherein the pivot is a hinge pivotally suspended within a corresponding pivot bearing of the immobile base portion.

4. The sonication device of claim 1, wherein the mount for the sample tube holder further comprises a height adjustment for adjusting positions of the at least two sample tubes in the sample tube holder on the z-axis.

5. The sonication device of claim 1, wherein the guiding rail comprises a sled.

6. The sonication device of claim 1, wherein the actuator is configured to apply a variable force to the sonotrode.

7. The sonication device of claim 6, wherein the actuator is configured to apply a force of 10 N, 50 N, 100 N, 500 N, 750 N, 1000 N, 2500 N, or 5000 N to the sonotrode.

8. The sonication device of claim 7, wherein the force is about 800 N.

9. The sonication device of claim 1, wherein the mount is configured to permit movement of the sample tube holder along the x-axis.

10. The sonication device of claim 1, wherein the sample tube holder is configured to permit movement of the at least two sample tubes within the sample tube holder along the x-axis.

11. A method for sonicating a biological sample contained in a sample tube using the sonication device of claim 1, the method comprising the following steps:
  a) in any order, inserting the at least two sample tubes into the sample tube holder, and inserting the sample tube holder into the mount;
  b) moving the sonotrode on the guiding rail along the y-axis towards the sample tube holder via the actuator until the at least two sonicating areas contact the side walls of the at least two sample tubes through the opening on the at least one side;
  c) applying a pre-defined force from the actuator via the sonotrode to the at least two sample tubes and/or the sample tube holder along the y-axis such that each of the at least two sonicating areas contacts the side wall of each of the at least two sample tubes and pushes the at least two sample tubes against an inner wall of the sample tube holder, thereby firmly holding the at least two sample tubes in place and adjusting positions of the at least two sample tubes along the x-axis by centering the at least two sample tubes with the concave surfaces comprised by the at least two sonicating areas, the movement of the sonotrode further causing a rotational movement of the sample tube holder about the x-axis until reaching an arresting point; and, d) applying ultrasound to the at least two sample tubes from the sonotrode through the contact areas between the at least two sonicating areas and the side wall of each of the at least two sample tubes.

12. A sonication device for sonicating one or more biological samples disposed in at least two sample tubes, each of the at least two sample tubes having an essentially round-shaped side wall, the sonication device comprising:
  a. a sample tube mount comprising (i) an immobile first portion; and (ii) a second portion comprising a pivot member and a base for holding a sample tube holder, wherein the second portion is pivotally suspended from the immobile first portion, and wherein the second portion is pivotable about the pivot member along an x-axis, wherein the sample tube holder comprises a support element having at least two concave surfaces, where each concave surface is configured to individually contact a side wall of each of the at least two sample tubes, and wherein the support element protrudes from a back wall of the sample tube holder;
  b. a sonotrode coupled to a guiding rail, the sonotrode comprising a transmittal unit having at least two sonicating areas, the at least two sonicating areas each comprising a concave surface, wherein the sonotrode is movable on the guiding rail along a y-axis toward or away from the sample tube holder, wherein the immobile first portion of the sample tube mount is coupled to a first end of the guiding rail such that an opening on at least one side of the sample tube holder faces the at least two sonicating areas of the sonotrode; and
  c. an actuator for moving the sonotrode along the guiderail;
  wherein the sample tube holder is configured to hold the at least two sample tubes in a position offset from the z-axis when the essentially round-shaped side wall of each of the at least two sample tubes is not in physical contact with the concave surfaces of the at least two sonicating areas of the sonotrode; and wherein the sample tube holder is configured to rotate counter-clockwise about the x-axis to a position substantially parallel with the z-axis when the essentially round-shaped side wall of each of the at least two sample tubes is in physical contact with the concave surfaces of the at least two sonicating areas of the sonotrode.

13. The sonication device of claim 12, wherein the sample tube holder is removable.

14. The sonication device of claim 12, wherein the pivot member comprises a hinge pivotally suspended within a corresponding pivot bearing of the immobile first portion.

15. The sonication device of claim 12, wherein the sample tube mount further comprises a height adjustment mechanism for adjusting positions along the z-axis of the at least two sample tubes in the sample tube holder.

16. The sonication device of claim 12, wherein the guiding rail comprises a sled.

17. The sonication device of claim 12, wherein the actuator is configured to apply a variable force to the sonotrode.

18. The sonication device of claim 12, wherein the sample tube holder is configured such that the at least two sample tubes are permitted to slide within the sample tube holder over the at least two concave surfaces of the support element along the x-axis as the concave surface of each of the at least two sonicating areas engages the essentially round-shaped side walls of each of the at least two sample tubes.

* * * * *